(12) United States Patent
Xu et al.

(10) Patent No.: US 9,993,182 B2
(45) Date of Patent: Jun. 12, 2018

(54) COMPUTER VISION SYSTEM FOR AMBIENT LONG-TERM GAIT ASSESSMENT

(71) Applicant: Conduent Business Services, LLC, Dallas, TX (US)

(72) Inventors: Beilei Xu, Penfield, NY (US); Hao Wu, Pittsford, NY (US); Wencheng Wu, Webster, NY (US); Robert P. Loce, Webster, NY (US)

(73) Assignee: Conduent Business Services, LLC, Dallas, TX (US)

( * ) Notice: Subject to any disclaimer, the term of this patent is extended or adjusted under 35 U.S.C. 154(b) by 0 days. days.

(21) Appl. No.: 15/283,629

(22) Filed: Oct. 3, 2016

(65) Prior Publication Data
US 2017/0238846 A1  Aug. 24, 2017

Related U.S. Application Data

(60) Provisional application No. 62/297,341, filed on Feb. 19, 2016.

(51) Int. Cl.
*G06K 9/00* (2006.01)
*A61B 5/11* (2006.01)
(Continued)

(52) U.S. Cl.
CPC ............ *A61B 5/112* (2013.01); *A61B 5/1128* (2013.01); *A61B 5/7275* (2013.01);
(Continued)

(58) Field of Classification Search
CPC ....... A61B 5/112; A61B 5/1128; A61B 5/117; A61B 5/7235; A61B 5/7275;
(Continued)

(56) References Cited

U.S. PATENT DOCUMENTS 6,231,527 B1 * 5/2001 Sol ..................... A61B 5/1038
348/143
7,084,998 B2   8/2006 Blair et al.
(Continued)

FOREIGN PATENT DOCUMENTS

JP      2010017447 A  *  1/2010

OTHER PUBLICATIONS

Felzenszwalb, Pedro F., Girshick, Ross B., McAllester, David, Ramanan, Deva, "Object Detection with Discriminatively Trained Part-Based Models", IEEE Transactions on Pattern Analysis and Machine Intelligence, vol. 32, No. 9, Sep. 2010.
(Continued)

*Primary Examiner* — Mekonen Bekele
(74) *Attorney, Agent, or Firm* — Fay Sharpe LLP (57) ABSTRACT

A method for gait analysis of a subject performed periodically over time to detect changes in one or more gait characteristics. The method includes detecting and identifying a subject and analyzing the gait of the subject on a plurality of occasions. Analyzing the gait of the subject includes, a detecting body parts, generating a joint model depicting the location of the at least one joint in each of the at least two frames, using the joint model to segment a gait cycle for the at least one joint, and comparing the gait cycle to a threshold value to detect abnormal gait.

16 Claims, 6 Drawing Sheets

(51) Int. Cl.
  G06T 7/00    (2017.01)
  G06K 9/62    (2006.01)
  G06K 9/46    (2006.01)
  A61B 5/00    (2006.01)
(52) U.S. Cl.
  CPC ..... *G06K 9/00348* (2013.01); *G06K 9/00362* (2013.01); *G06K 9/4604* (2013.01); *G06K 9/6202* (2013.01); *G06T 7/0081* (2013.01)
(58) Field of Classification Search
  CPC ........... G06K 9/00342; G06K 9/00348; G06K 9/00362; G06K 9/00885; G06K 9/4604; G06K 9/6202; G06T 7/0042; G06T 7/0081; G06T 7/0097; G06T 7/20; G06T 2207/10004
  See application file for complete search history.

(56) References Cited

U.S. PATENT DOCUMENTS

| | | | |
|---|---|---|---|
| 7,227,893 B1 | 6/2007 | Srinivasa | |
| 7,330,566 B2 | 2/2008 | Cutler | |
| 7,660,439 B1 | 2/2010 | Lu | |
| 8,073,521 B2 | 12/2011 | Liew | |
| 8,154,644 B2 | 4/2012 | Thorn | |
| 8,246,354 B2 | 8/2012 | Chu | |
| 8,300,890 B1 | 10/2012 | Gaikwad | |
| 8,373,753 B2 | 2/2013 | Cheng | |
| 8,514,236 B2 | 8/2013 | Kobla | |
| 8,854,182 B2 | 10/2014 | Lobean | |
| 9,700,242 B2 * | 7/2017 | Utsunomiya | A61B 5/1127 |
| 2004/0228503 A1 | 11/2004 | Cutler | |
| 2009/0306801 A1 * | 12/2009 | Sivak | A61F 5/0111 700/98 |
| 2013/0218053 A1 * | 8/2013 | Kaiser | A61B 5/1123 600/595 |
| 2014/0261887 A1 * | 9/2014 | Groot | G01S 7/415 141/383 |
| 2014/0358040 A1 * | 12/2014 | Kim | A61B 5/112 600/595 |
| 2015/0173652 A1 * | 6/2015 | Brunner | A61B 5/112 482/7 |
| 2015/0196231 A1 * | 7/2015 | Ziaie | A61B 5/112 600/595 |
| 2017/0202724 A1 * | 7/2017 | De Rossi | A61H 3/00 |
| 2017/0238846 A1 * | 8/2017 | Xu | A61B 5/112 |
| 2017/0243057 A1 * | 8/2017 | Wu | G06K 9/00348 |
| 2017/0243354 A1 * | 8/2017 | Tafazzoli | G06T 7/0042 |
| 2017/0296116 A1 * | 10/2017 | McCarthy | A61B 5/486 |

OTHER PUBLICATIONS

Tomasi, Carlo, Kanade, Takeo, "Detection and Tracking of Point Features", Computer Science Department, Carnegie Mellon university, Apr. 1991.
Xu, Xin, Tang, Jinshan, Zhang, Xiaolong, Liu, Xiaoming, Zhang, Hong, Qiu Yimin, "Exploring Techniques for Vision Based Human Activity Recognitino: Methods, Systems, and Evaluation", Sensors 2013, 13, 1635-1650.
Park, Dennis, Ramanan, Deva, "N-best maximal decoders for part models", International Conference on Computer Vision (ICCV) Barcelona, Spain, pp. 2627-2634, Nov. 2011.
Wang, Heng, Klaser, Alexander, Schmid, Cordelia, Cheng-Lin, Liu, "Action Recognition by Dense Trajectories", CVPR 2011—IEEE Conference on Computer Vision & Pattern Recognition, Jun. 2011, pp. 3169-3176.
"Stone, Erik E., Skubic, Marjorie,"Capturing Habitual, in-Home Gait Parameter Trends Using an Inexpensive Depth Camera, 34th Annual International Conference of IEEE EMBS, Aug. 28-Sep. 1, 2012, pp. 5106-5109.
Sisto, Sue Ann, "An Overview of the Value of Information Resulting from Instrumented Gait Analysis for the Physical Therapist", RRDS Gait Analysis in the Science of Rehabilitation.
Park, Kiwon, Dissertation: "Quantitative Assessment of Human Gait Patterns Using Biomechanical and Dynamical Tools", University of Illinois, 2012.
Tafazzoli, F, Xu, B., Wu, W., Loce, R., "Automatic Frontal-View Gait Segmentation for Abnormal Gait Quantification,", U.S. Appl. No. 15/283,603, filed Oct. 3, 2016.
Hamdoun, Omar, Moutarde, Fabien, Stanciulescu, Bogdan, Steux Bruno, "Person re-identification in multi-camera system by signature based on interest point descriptors collected on short video sequences", 2nd ACM/IEEE International Conference on Distributed Smart Cameras (ICDSC-08), Sep. 2008, Stanford, Palo Alto, US.
Johansson, Gunnar, "Visual perception of biological motion and a model for its analysis", Perception & Psychophysics, 1973, vol. 14, No. 2, 201-211.
Mouta, Sandra, Santos, Jorge, Rybarczyk, Yves, "Visual perception of biological motion direction and velocity: global and local factors", Dept. of Psychology, I.E.P., University of Minho.
Nixon, Mark S., Carter, John N., "Advances in Automatic Gait Recognition", School of Electronics and Computer Science, University of Southampton.
Wang, Jin, She, Mary, Nahavandi, Saeid, "A Review of Vision-based Gait Recognition Methods for Human Identification", 2010 Digital Image Computing: Techniques and Applications, pp. 320-327.
Benabdelkader, Chiraz, Cutler, Ross; David, Larry, "Stride and Cadence as a Biometric in Automatic Person Identification and Verification", Automatic Face and Gesture Recognition, 2002. Proceedings. Fifth IEEE International Conference on IEEE, 2002.
Bouchrika, Imed, "Evidence Evaluation of Gait Biometrics for Forensic Investigation", Multimedia Forensics and Security. Springer International Publishing, 2017. 307-326.
Martín-Félez, Raúl; MollinedaJavier, Ramón A., Sánchez, Salvador, "Human Recognition Based on Gait Poses (Pattern Recognition and Image Analysis)", Iberian Conference on Pattern Recognition and Image Analysis IbPRIA 2011: Pattern Recognition and Image Analysis pp. 347-354.
Hoeger, Werner W.K., Bond, Laura, Ransdell, Lynda, Shimon, Jane M., Merugu, Sunitha, "One-Mile Step Count at Walking and Running Speeds", ACSM's Health & Fitness Journal vol. 12, No. 1 (2008), pp. 14-19.
Mark S. Nixon, Tieniu Tan, Rama Chellappa, Human Identification Based on Gait, Springer, 2006, Title page and p. 1, https://books.google.com/books?id=tD42mXCGRGcC&pg=PR4&lpg=PR4&dq=Mark+S.+Nixon,+Tieniu+Tan,+Rama+Chellappa,+%E2%80% 9CHuman+Identification+Based+on+Gait%E2%80%9D&source=bl&ots=YDiW8WA2Fx&sig=KoL7rtlochXoo EhhBZM8ulU8C6w&hl=en&sa=X&ved= 0ahUKEwjH47_mzNfVAhXCgFQKHXNmD-UQ6AEIUDAJ#v=onepage&q=Mark%20S.%20Nixon%2C%20Tieniu%20Tan% 2C%20Rama%20Chellappa%2C%20%E2%80%9CHuman %20Identification%20Based%20on%20Gait%E2%80%9D&f=false.
Yang, Yi, Ramanan, Deva, "Articulated Human Detection with Flexible Mixtures-of-Parts", IEEE Transactions on Pattern Analysis and Machine Intelligence (PAMI), vol. 61, No. 1, pp. 55-79, 2013.
Zhou, Xiaowei, Leonardos, Spyridon, Hu, Xiaoyan, Daniilidis, Kostas, "3D Shape Estimation from 2D Landmarks: A Convex Relaxation Approach", IEEE Conference on Computer Vision and Pattern Recognition (CVPR), pp. 259-267, 2015.
MoCap: Carnegie Mellon University Motion Capture database. http://mocap.cs.cmu.edu/.

* cited by examiner

COMPUTER VISION SYSTEM FOR AMBIENT LONG-TERM GAIT ASSESSMENT

CROSS REFERENCE TO RELATED PATENTS AND APPLICATIONS

This application claims priority to and the benefit of the filing date of U.S. Provisional Patent Application Ser. No. 62/297,341, filed Feb. 19, 2016, which application is hereby incorporated by reference.

BACKGROUND

Human gait analysis and assessment involves challenging issues due to the highly flexible structure and self-occlusion of the human body. These issues mandate using complicated processes for the measurement and analysis. Typically, gait analysis is performed in a gait laboratory that uses a combination of technologies to evaluate the biomechanics of gait: a marker-based motion capture system, force plates, an electromyography system, and a pressure sensitive electronic walkway. The systems used in a gait laboratory provide accurate descriptions and models of gait. However, these expensive systems must be installed in appropriate rooms and can only be operated by specially trained personnel in a clinical setting. However, a clinical visit is not only costly, but also ineffective for many applications because 1) the clinical walkway is not representative of the complex environment within which a subject must function; and 2) the symptoms of many diseases can vary greatly from time-to-time.

Among the most widely used and studied techniques for gait analysis and assessment utilize wearable sensors such as those based on accelerometers and gyroscopes. Many wearable systems have demonstrated accuracy and precision, but suffer from limitations such as short battery life, the need to download the data or introduce additional hardware for wireless data collection, and the inconvenience of both a wearable device and having to remember to wear a device. For these reasons, wearable devices are currently inadequate for long-term, in-home, unobtrusive monitoring.

Gait characteristics have been linked with a variety of medical conditions in clinical research. A change in the gait profile over time may indicate a disease state change or a person is at risk of falling. Hence, monitoring walking patterns on a daily basis using smart-home technologies, such as camera monitors and/or walking-sensors, can provide essential information on the change of functional status of a subject.

Thus, continuous gait assessment would provide clear advantages over the clinic-based tests, especially for seniors living in nursing homes, while monitoring their regular day-to-day activities, as walking is one of the most natural physical activities and can be conveniently and easily accommodated into an older adult's routine. Such a monitoring system when combined with advanced algorithms to detect subtle gait changes can potentially be used to identify diagnostic measures that are predictors of fall-prone elderly or disease status change so that effective interventions can be made in a timely manner to prevent or reduce severe health outcomes.

There is, therefore, a clear need for an inexpensive, unobtrusive and easy-to-use system, which allows continuous and quantitative analysis of gait patterns outside the lab.

INCORPORATION BY REFERENCE

The following references, the disclosures of which are incorporated by reference herein in their entireties, and filed concurrently, are mentioned:

U.S. application Ser. No. 15/283,603, filed Oct. 3, 2016, by Tafazzoli et al., entitled "AUTOMATIC FRONTAL-VIEW GAIT SEGMENTATION FOR ABNORMAL GAIT QUANTIFICATION"; and, U.S. application Ser. No. 15/283,663, filed Oct. 3, 2016, by Wu et al., entitled "SYSTEM AND METHOD FOR AUTOMATIC GAIT CYCLE SEGMENTATION".

The following reference, the disclosure of which is incorporated by reference herein in its entirety, is mentioned:

U.S. application Ser. No. 14/963,602, filed Dec. 9, 2015, by Bernal, et al., entitled "COMPUTER-VISION-BASED GROUP IDENTIFICATION".

BRIEF DESCRIPTION

In accordance with one aspect, a computer-implemented method for gait analysis of a subject comprises obtaining visual data from an image capture device, the image capture device being positioned in front of or behind at least one walking subject, the visual data comprising at least two image frames of the at least one walking subject over a period of time walking toward or away from the image capture device, the at least two image frames capturing at least a portion of the gait of the at least one walking subject, analyzing the visual data to determine the identity of the at least one walking subject. For each identified walking subject: segmenting one or more gait cycles of the identified walking subject, detecting at least one gait feature in the one or more gait cycles, comparing the at least one gait feature to at least one of the following to detect an abnormal gait: a threshold value or a history of gait cycles of the identified walking subject. The foregoing steps are repeated over a period of time to generate a gait profile for each identified walking subject.

The segmenting one or more gait cycles can include detecting within the at least two images body parts as two-dimensional landmarks using a pose estimation algorithm on each of the at least two frames, and generating a joint model depicting the location of the at least one joint in each of the at least two frames. The method can further include analyzing the gait profile to detect at least one trend in at least one gait cycle. The at least one trend can include a change in gait length, time or angle. The method can also include, prior to generating the joint model, estimating a three-dimensional shape of the subject using the two-dimensional landmarks, and estimating the at least one joint location based on the three-dimensional shape. The joint model can include a deformable parts model. The at least one joint can include an ankle, a knee, a hip, or other joint. The gait cycle can include a distance between two consecutive peaks in a trajectory of a joint. The gait cycle can include a distance between consecutive peaks in an angle of a joint or body part.

In accordance with another aspect, a system for gait analysis of a subject comprises an image capture device operatively coupled to a data processing device and positioned in front of or behind a region interest wherein a plurality of subjects periodically walk, a processor-usable medium embodying computer code, said processor-usable medium being coupled to said data processing device, said computer code comprising instructions executable by said data processing device and configured for: monitoring a region of interest with the image capture device wherein a plurality of subjects periodically walk, detecting activity within the region of interest corresponding to at least one walking subject, obtaining visual data from the image capture device, the image capture device being positioned in front of or behind at least one walking subject, the visual data comprising at least two image frames of the at least one walking subject over a period of time walking toward or away from the image capture device, the at least two image frames capturing at least a portion of the gait of the at least one walking subject, and analyzing the visual data to determine the identity of the at least one walking subject. For each identified walking subject: segmenting one or more gait cycles of the identified walking subject, detecting at least one gait feature in the one or more gait cycles comparing the at least one gait feature to at least one of the following to detect an abnormal gait: a threshold value or a history of gait cycles of the identified walking subject. The foregoing steps are repeated over a period of time to generate a gait profile for each identified walking subject.

The segmenting one or more gait cycles can include detecting within the at least two images body parts as two-dimensional landmarks using a pose estimation algorithm on each of the at least two frames, and generating a joint model depicting the location of the at least one joint in each of the at least two frames. The method can further include analyzing the gait profile to detect at least one trend in at least one gait cycle. The at least one trend can include a change in gait length, time or angle. The method can also include, prior to generating the joint model, estimating a three-dimensional shape of the subject using the two-dimensional landmarks, and estimating the at least one joint location based on the three-dimensional shape. The joint model can include a deformable parts model. The at least one joint can include an ankle, a knee, a hip, or other joint. The gait cycle can include a distance between two consecutive peaks in a trajectory of a joint. The gait cycle can include a distance between consecutive peaks in an angle of a joint or body part.

In accordance with another aspect, a non-transitory computer-usable medium for gait analysis of a subject, said computer-usable medium embodying a computer program code, said computer program code comprising computer executable instructions configured for: obtaining visual data from the image capture device, the image capture device being positioned in front of or behind at least one walking subject, the visual data comprising at least two image frames of the at least one walking subject over a period of time walking toward or away from the image capture device, the at least two image frames capturing at least a portion of the gait of the at least one walking subject, and analyzing the visual data to determine the identity of the at least one walking subject. For each identified walking subject: segmenting one or more gait cycles of the identified walking subject, detecting at least one gait feature in the one or more gait cycles, comparing the at least one gait feature to at least one of the following to detect an abnormal gait: a threshold value or a history of gait cycles of the identified walking subject. The foregoing steps are repeated over a period of time to generate a gait profile for each identified walking subject.

The segmenting one or more gait cycles can further include detecting within the at least two images body parts as two-dimensional landmarks using a pose estimation algorithm on each of the at least two frames, and generating a joint model depicting the location of the at least one joint in each of the at least two frames.

DETAILED DESCRIPTION

Aspects of the present disclosure are directed to achieving objective evaluation of different gait parameters by applying computer vision techniques using existing monitoring systems without much additional cost or equipment, and performing an assessment during a user's daily activity without the requirement to wear a device. Computer vision approaches can allow simultaneous, in-depth analysis of a higher number of parameters than current wearable systems. Unlike wearable sensors, they are not restricted by power consumption. The algorithms can provide a consistent, objective measure, which reduces error and variability incurred by subjective techniques.

The present disclosure sets forth a computer vision approach for long-term gait assessment with the capability to leverage existing or common ambient video monitoring systems that are used in many environments such as assisted living centers and nursing homes. The system is non-intrusive to the subjects being monitored, but can potentially incorporate a variety of information from other sources such as wearable sensors. The proposed system includes one or more of the following components (note that some can be components that are parallel to each other in the process pipeline): 1) image acquisition and system activation; 2) subject detection and identification; 3) walking activity detection and recognition; 4) gait parameter extraction; 5) fine grained gait quantification and trend detection/prediction.

Passive video monitoring has been used in various environments for various reasons. For example, in nursing homes, passive video monitoring not only ensures the safety of residents, e.g., fall detection, but also provides a data source to monitor the health conditions of a resident to enable early interventions. In those environments, the activities of an individual subject can be captured in a variety of settings, e.g., hallways, dining rooms, etc., under a variety of conditions, daytime, viewing angles, camera settings.

Figure 1:
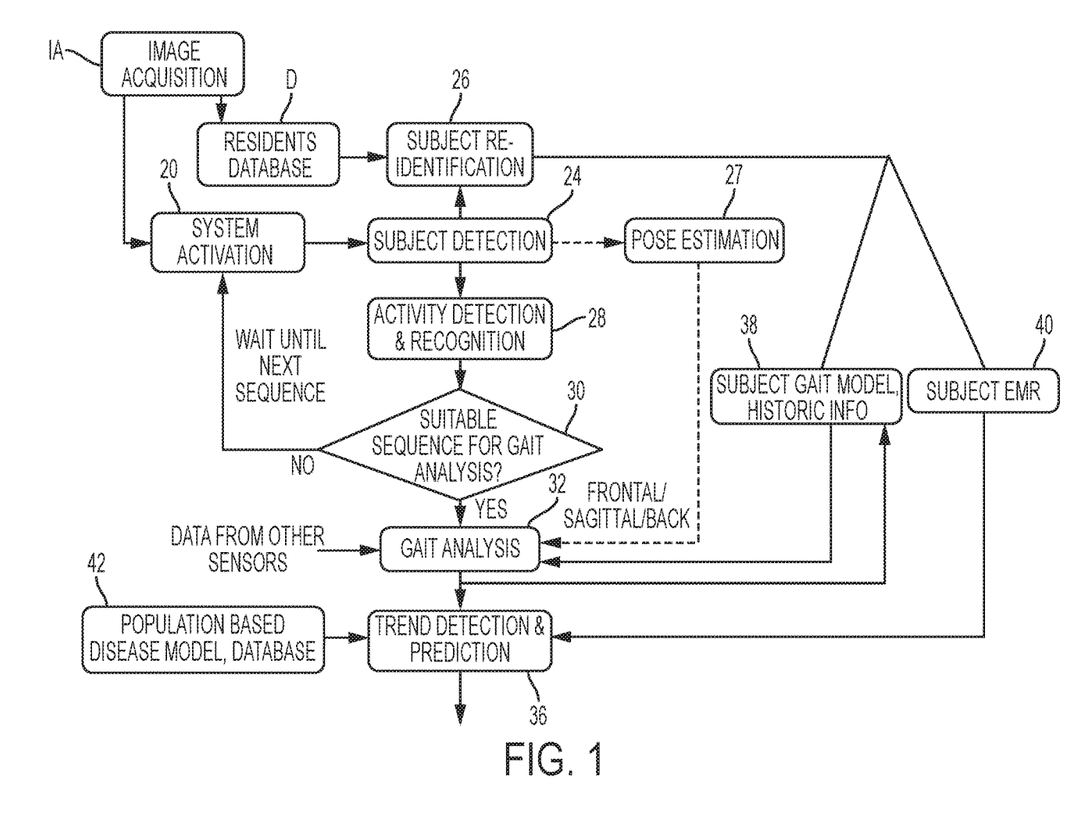
FIG. 1 is a flowchart of an exemplary method in accordance with the present disclosure.

With reference to FIG. 1, an exemplary method 10 in accordance with an embodiment of the present disclosure is illustrated. The exemplary method 10 includes one or more of the following steps:

1) System Activation or Video Segmentation—Step 20

For example, recording videos or identify the starting/ending points of video segments that can be used for gait analysis. An image acquisition step IA includes feeding images and/or video to both the system for processing (as described herein) as well as a residents database D for identification of residents or other individuals within the images and/or video.

2) Subject Detection and Re-Identification—Steps 24 and 26 (Optionally, Pose Estimation)

For example, verifying an object in the image(s) is a human being and identifying/re-identifying the subject using a database D (e.g., residents in a particular nursing home); optionally, the system can perform pose estimation at step 27 (e.g., frontal/sagittal/back views of the subject) so that proper gait analysis techniques can be employed.

3) Walking Activity Detection and Recognition—Step 28

For example, from the initialized subject, verifying the activity being observed is walking and, if so, determine if the sequence is suitable for gait analysis in step 30 (e.g., no occlusion of subject body, small viewing angle change, duration of walking is sufficient (e.g., 20 seconds or 3~5 walking cycles), etc.). If the sequence is not suitable for gait analysis, the method reverts to step 20.

4) Gait Parameter Extraction—Step 32

For example, if the sequence is suitable for gait analysis, determining gait parameters, e.g., stride duration/length, etc.;

5) Fine Grained Quantification and Trend Detection/Prediction—Step 36

For example, from a set of gait parameters, a subject's gait pattern will be quantified (e.g., severity of disease state, cause of abnormality) and compared with the historical data 38 from the subject, either through gait parameters, or a gait model. From the historical data 38 and the newly acquired data, any change of gait pattern is detected (e.g., level of severity) or the trend of the change is estimated; optionally, the newly acquired date can be compared to a patient electronic medical record 40 and/or with a database 42 for a specific disease to determine if the status requires medical attention.

Figure 2:
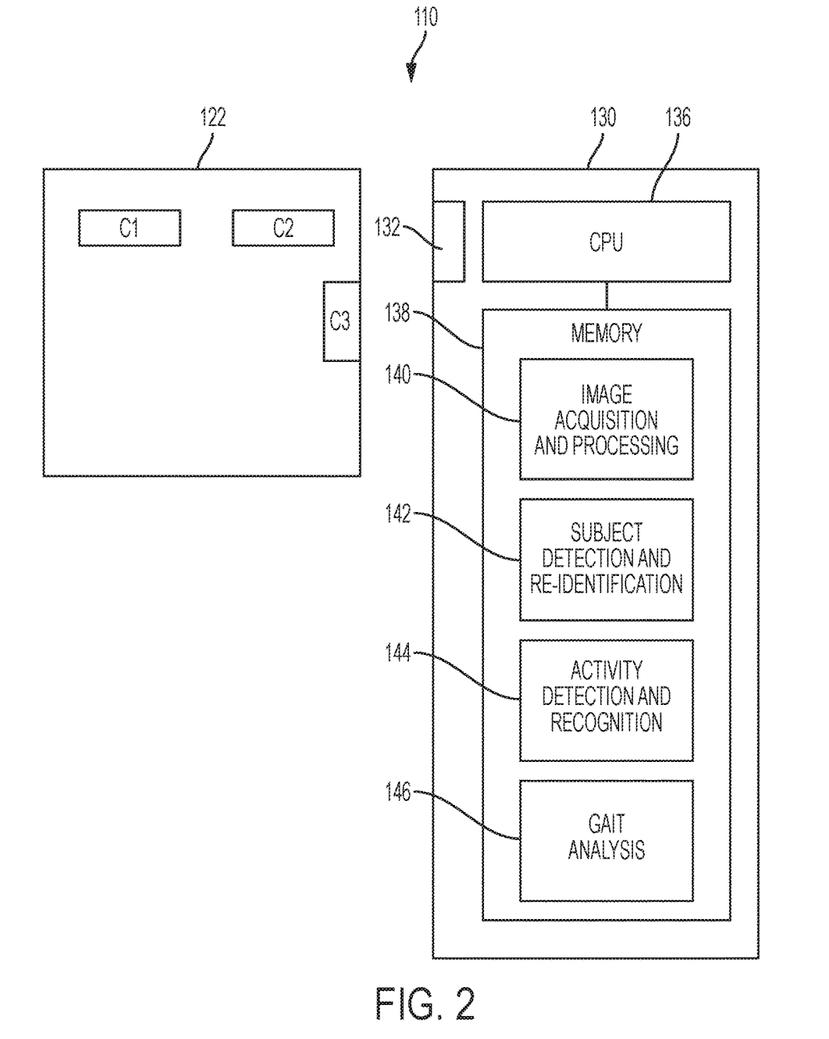
FIG. 2 is a schematic block diagram of an exemplary system in accordance with the present disclosure.

In FIG. 2, an exemplary system 110 is illustrated in block diagram form in connection with a patient space 122 such as a hallway, waiting room, or the like. It will be appreciated that patient space 122 is exemplary, and that the system 110 can be implemented in virtually any location or setting (e.g., public or private spaces, etc.) provided suitable images of a subject approaching and/or departing can be obtained. In the exemplary embodiment, a plurality of cameras C1, C2 and C3 are positioned at different locations within the patient space 122. However, any number of cameras can be utilized.

The cameras C1, C2 and C3 are connected to a computer 130 and supply visual data comprising one or more image frames thereto via a communication interface 132. It will be appreciated that the computer 130 can be a standalone unit configured specifically to perform the tasks associated with the aspects of this disclosure. In other embodiments, aspects of the disclosure can be integrated into existing systems, computers, etc. The communication interface 132 can be a wireless or wired communication interface depending on the application. The computer 130 further includes a central processing unit 136 coupled with a memory 138. Stored in the memory 138 are various modules including an image acquisition module 140, a subject detection and identification module 142, a walking activity detection and recognition module 144 and a gait analysis module 146. Visual data received from the cameras C1, C2 and C3 can be stored in memory 38 for processing by the CPU 36 in accordance with this disclosure. It will further be appreciated that the various modules can be configured to carryout the functions described in detail in the following paragraphs.

Although videos are constantly recorded in video surveillance systems, it is useful and efficient to identify interesting segments, e.g., a segment when an activity happens. There are multiple technologies that are applicable for this purpose such as various triggering mechanism based on motion, WIFI or other types of sensors. The most widely used and simple computer vision approach is through motion/background detection. For example, with minimum computational cost frame-to-frame differencing can reveal new objects entering a scene. The corresponding frame when an event happens will be labelled, either for initiating real-time processing or for later retrieval of the segment. An exemplary method for gait segmentation is set forth in concurrently filed U.S. application Ser. No. 15/283,663, filed Oct. 3, 2016, by Wu et al., entitled "SYSTEM AND METHOD FOR AUTOMATIC GAIT CYCLE SEGMENTATION". Since the system and methods of the present disclosure do not have to be operated in real time, manual selection and segmentation is also applicable.

Figure 3:
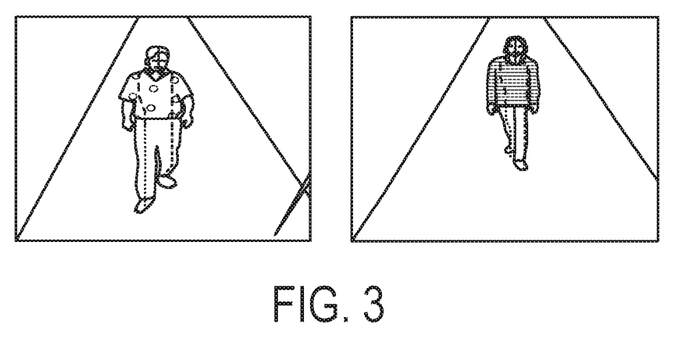
FIG. 3 shows a pair of images with detected body parts superimposed thereon.

Once a moving region is detected in a scene, the moving object/objects need to be detected and recognized. In one scenario, only human subjects are of interest. Therefore, a human detector can be applied to the moving regions to detect human objects. One of the most commonly used techniques is the deformable part model (DPM) based approach examples of which are shown as the two images in FIG. 3. DPM represents highly variable objects using mixtures of multiscale deformable part models. These models are trained using a discriminative method that only requires bounding boxes for the objects in an image. Its output can also be used for pose estimation, which is discussed below.

For the purpose of long-term gait assessment, the identity of the detected subject can be recognized/identified so his/her gait information can be compared to their own information over time or with others who suffer from the same disease. As in this long-term monitoring application, the person usually has already been observed somewhere else in the network of cameras, or elsewhere previously. To retrieve their identity is commonly known as "person re-identification." Re-identification algorithms have to be robust even in challenging situations caused by differences in camera viewpoints and orientations, varying lighting conditions, pose variability of persons, and change in appearance of clothes.

There are two major categories within the field of re-identification. A first category of person re-identification methods relies on biometric techniques (such as face or gait recognition) and the second category uses only global appearance/signatures such as color histograms, texture characteristics, or panoramic model from multi-view. More recently some approaches have proposed the use of matching of interest points for establishing correspondence between objects. While gait analysis from video does not require viewing a face, facial recognition is one image-based biometric methods that can be used to re-identify a person. The camera viewing the gait could view the face, or the face could be viewed with a different camera. Other non image-based methods, such as information taken from key entry cards and enter/exit from particular doors.

Optionally, subject pose, e.g., frontal/sagittal view, is identified. In this disclosure, the algorithms for gait analysis can be different when the subject is viewed from different perspectives, such as side or front. For example, from the side, it is easier to detect the knee bend and stoop posture than from front, while it is easier to detect posture asymmetries from the frontal view. There are additional reasons why detecting pose is useful. A fundamental one is that often that the pose, or a pose sequence, characterizes a person's attitude or action (i.e., walking). Moreover, 2D human pose estimation is often the first step in determining 3D human pose from individual frames, which can yield improved gait analysis. The aforementioned DPM model has also been used for pose estimation. This step can be combined with subject identification or reuse features extracted from subject identification to save overall system level computational cost.

Once a human object is detected and identified, it will be tracked within the view of the camera/camera networks and his/her activity will be analyzed. Automatic activity recognition is an important research direction in surveillance vision analysis. In one embodiment, a walking sequence needs to be detected and identified from a sequence of frames of a particular subject identified in step 28. A popular approach pursued by vision researchers for action recognition is to utilize the motion of the human subject, where the motion can be quantified in terms of optical flow or feature trajectories computed from the sequence of images depicting the action. Dense sampling has shown to improve results over sparse interest points for image classification. The same has been observed for action recognition as well, where dense sampling at regular positions in space and time outperforms state-of-the-art space-time interest point detectors. The trajectories are obtained by tracking densely sampled points using optical flow fields. The number of tracked points can be scaled up easily, as dense flow fields are already computed. Furthermore, global smoothness constraints are imposed among the points in dense optical flow fields, which results in more robust trajectories than tracking or matching points separately. In addition to recognizing the walking sequence, the system can also evaluate whether the sequence is suitable for gait analysis (step 30). Although work has been done to recognize various simple actions from very short video segments (5~7 frames), gait analysis generally requires a minimum of 3~5 cycles. Furthermore, the subject should not be partially occluded (such as the lower extremities) or have significant pose change during the sequence (compared to the database). The aforementioned DPM-based pose detection method can also be applied to the tracked person and used to detect a suitable walking sequence for gait analysis.

Figure 4:
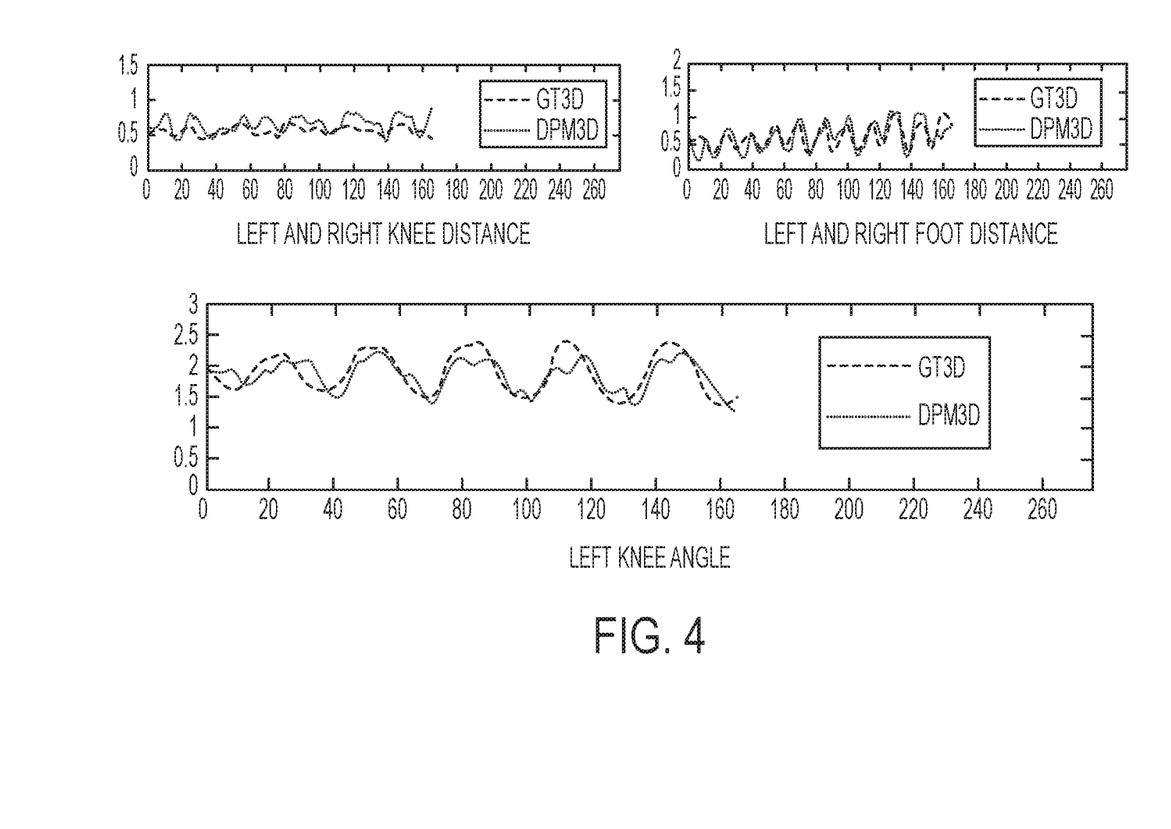
FIG. 4 graphically illustrates calculated features from a reconstructed 3D model of DPM landmarks (DPM3D) compared with the features of a 3D model built based on manually annotated joints (GT3D)

Gait parameters can then be extracted from the walking sequence. For example, FIG. 4 plots three different features as they are observed over multiple cycles that occur in time. Hence, they can be considered different representations of gait cycles. Each plot shows two trajectories, one labeled GT3D is based on the Ground Truth taken from video where body joints were manually labeled. The other labeled DPM3D is based on the Deformable Part Model applied to the video. For instance, in the lower plot the angle of the left knee is plotted against time (equivalently, video frame number), where one gait cycle is observed within the distance between two consecutive peaks. Foot-to-foot distance is plotted in the upper right plot, where one gait cycle is observed across three consecutive peaks. The plot on the upper left of FIG. 4 shows the trajectory of another feature; the distance between the left and right knee. While plotting this feature does not show the gait cycle so clearly, this feature along with others can be useful in extracting other information about gait. From all or a selected subset of features, one can segment out gait cycles (peak-to-peak distances) from the sequences. The segmentation derived from one or more set of features may be applied to other features to assist in segmenting the cycles for those features. From the segmented gait cycles, a set of metrics can be estimated such as stride duration, stride length, cadence step width, sway, as well as others that have been shown clinically to be good indicators of various diseases injuries and frailty. The estimated set of metrics along with other features can then be employed for abnormal gait quantification depending on the application.

Figure 5:
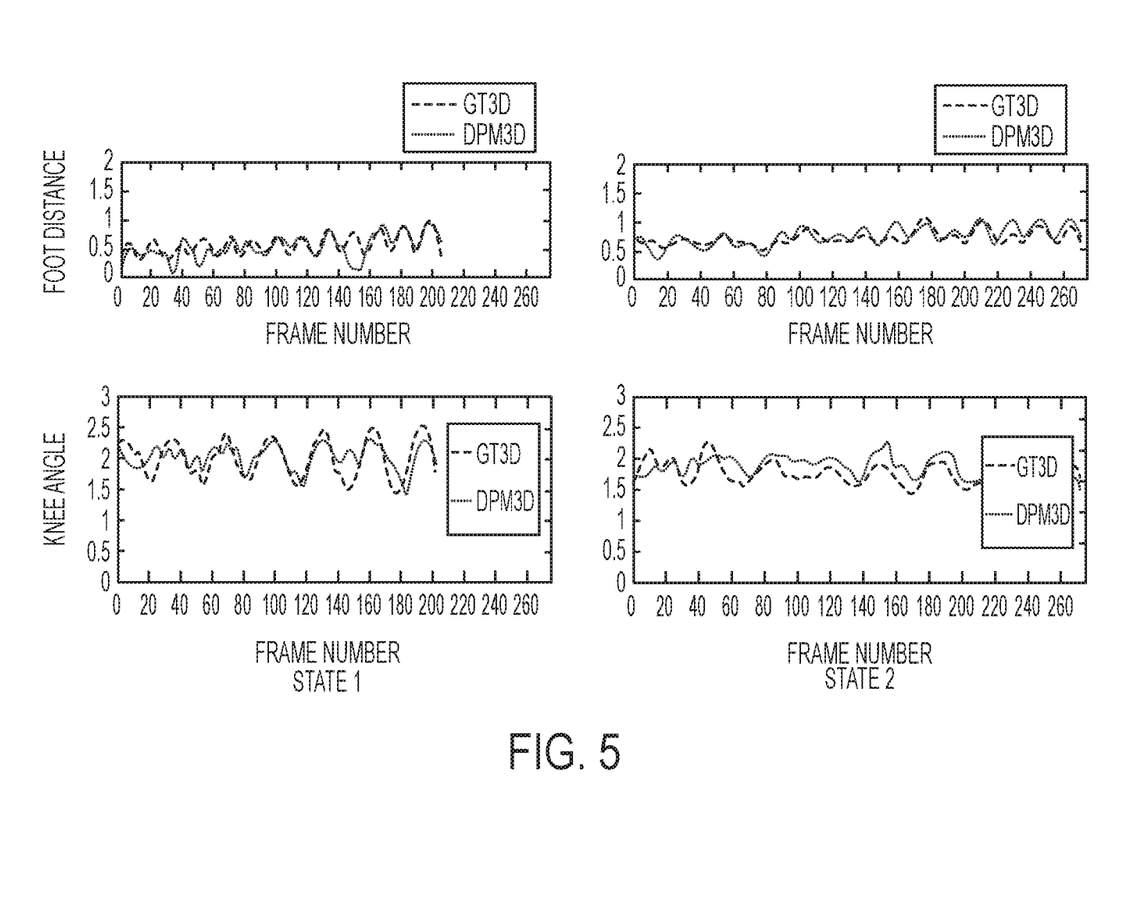
FIG. 5 graphically illustrates a comparison between two main features displayed in FIG. 4 (foot distance and knee angle), for two different experiments of the same subject, for both the calculated DPM3D and manually annotated joints GT3d.

FIG. 5 displays a comparison between foot distance and knee angle, for two states of the same subject where a change in gait was induced by having the subject wear an ankle weight. One can clearly see the changes in stride duration (horizontal axis) by increasing the weights. These changes are summarized in FIG. 6 for the variation of stride duration of the same subject.

Figure 6:
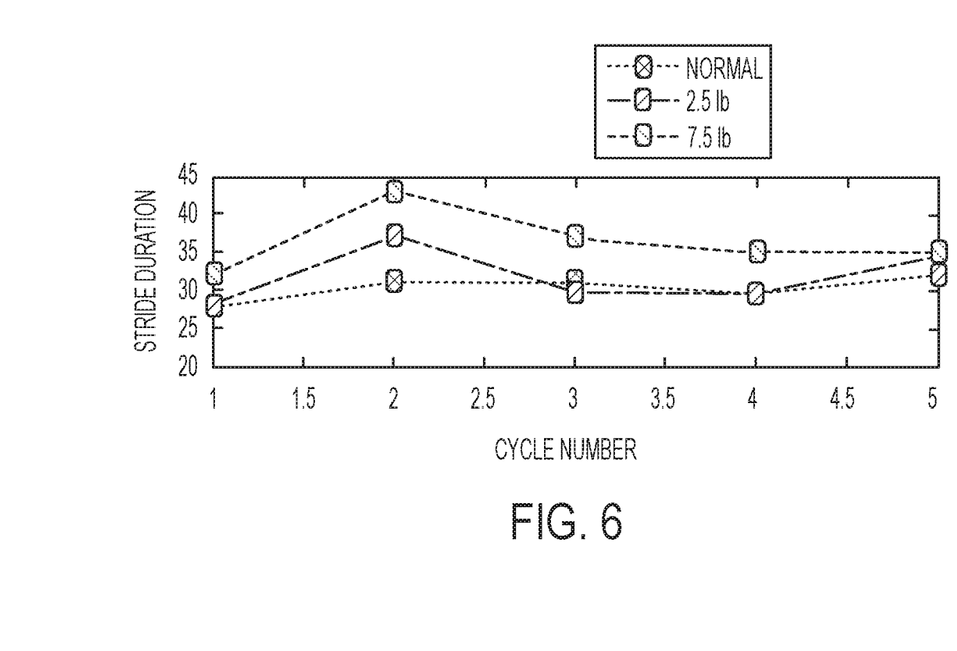
FIG. 6 graphically illustrates the variation of stride duration of the subject for the different conditions of FIG. 5.

The extracted gait parameters are then compared with the subjects gait parameters from the database. Change-Point/trend/anomaly detection is performed to identify any statistically significant change that requires medical attention. In addition, the gait parameter can be compared to a database that consists of gait descriptors for different diseases. FIG. 6 shows a subject's stride duration changes over the time (under different weight settings in the experiment). Stride-to-stride variation clearly shows the trend of this subject's gait changes. As weight increases, the variability also increases. A change in variability over a number of cycles is also an indication of a gait change.

It should be appreciated that the present disclosure provides:
A system and method for long-term gait assessment in the wild
Incorporation of personalized gait database, model as well as population-based disease model
Multimodal data fusion/reasoning for gait assessment
Enabled ambient monitoring via existing surveillance systems
Enabled long-term assessment via subject re-identification
Non-intrusive to subjects It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A computer-implemented method for gait analysis of a subject comprising:
   obtaining visual data from a single frontal view image capture device, the image capture device being positioned in front of at least one walking subject, the image capture device including a camera mounted in an elongate hallway in which the subject can walk towards the camera, said visual data including a frontal view of the subject approaching the camera, the visual data comprising at least two image frames of the at least one walking subject over a period of time walking toward the image capture device, the at least two image frames capturing at least a portion of the gait of the at least one walking subject;
   analyzing the visual data to determine the identity of the at least one walking subject;
   for each identified walking subject:
      segmenting one or more gait cycles of the identified walking subject, the segmenting including detecting within the at least two images body parts as two-dimensional landmarks using a pose estimation algorithm on each of the at least two frames, generating a joint model depicting the location of the at least one joint in each of the at least two frames, and using the joint model to segment the one or more gait cycles;

detecting at least one gait feature in the one or more gait cycles;

comparing the at least one gait feature to at least one of the following to detect an abnormal gait: a threshold value or a history of gait cycles of the identified walking subject;

repeating the foregoing steps over a period of time to generate a gait profile for each identified walking subject; and analyzing the gait profile to detect at least one trend in at least one gait cycle over time.

2. The computer-implemented method for gait analysis of a subject as set forth in claim 1, wherein the at least one trend includes a change in stride length, duration or cadence.

3. The computer-implemented method for gait analysis of a subject as set forth in claim 1, further comprising, prior to generating the joint model, estimating a three-dimensional shape of the subject using the two-dimensional landmarks, and estimating the at least one joint location based on the three-dimensional shape.

4. The computer-implemented method for gait analysis of a subject as set forth in claim 1, wherein the joint model includes a deformable parts model.

5. The computer-implemented method for gait analysis of a subject as set forth in claim 1, wherein the at least one joint includes an ankle, a knee, a hip, or other joint.

6. The computer-implemented method for gait analysis of a subject as set forth in claim 5, wherein the gait cycle includes a distance between two consecutive peaks in a trajectory of a joint.

7. The computer-implemented method for gait analysis of a subject as set forth in claim 5, wherein the gait cycle includes a distance between consecutive peaks in an angle of a joint or body part.

8. A system for gait analysis of a subject comprising:

an image capture device operatively coupled to a data processing device and positioned in front of or behind a region interest wherein a plurality of subjects periodically walk, the image capture device including a camera mounted in an elongate hallway in which the plurality of subjects can walk towards the camera, said visual data including a frontal view of the subject approaching the camera;

a processor-usable medium embodying computer code, said processor-usable medium being coupled to said data processing device, said computer code comprising instructions executable by said data processing device and configured for:

monitoring a region of interest with the image capture device wherein a plurality of subjects periodically walk;

detecting activity within the region of interest corresponding to at least one walking subject;

obtaining visual data from the image capture device, the image capture device being positioned in front of at least one walking subject, the visual data comprising at least two image frames of the at least one walking subject over a period of time walking toward the image capture device, the at least two image frames capturing at least a portion of the gait of the at least one walking subject;

analyzing the visual data to determine the identity of the at least one walking subject;

for each identified walking subject:

segmenting one or more gait cycles of the identified walking subject, the segmenting including detecting within the at least two images body parts as two-dimensional landmarks using a pose estimation algorithm on each of the at least two frames, generating a joint model depicting the location of the at least one joint in each of the at least two frames, and using the joint model to segment the one or more gait cycles;

detecting at least one gait feature in the one or more gait cycles;

comparing the at least one gait feature to at least one of the following to detect an abnormal gait: a threshold value or a history of gait cycles of the identified walking subject;

repeating the foregoing steps over a period of time to generate a gait profile for each identified walking subject.

9. The system for gait analysis as set forth in claim 8, further comprising analyzing the gait profile to detect at least one trend in at least one gait cycle.

10. The system for gait analysis as set forth in claim 9, wherein the at least one trend includes a change in gait length, duration or angle.

11. The system for gait analysis as set forth in claim 8, further comprising, prior to generating the joint model, estimating a three-dimensional shape of the subject using the two-dimensional landmarks, and estimating the at least one joint location based on the three-dimensional shape.

12. The system for gait analysis as set forth in claim 8, wherein the joint model includes a deformable parts model.

13. The system for gait analysis as set forth in claim 8, wherein the at least one joint includes an ankle, a knee, a hip, or other joint.

14. The system for gait analysis as set forth in claim 13, wherein the gait cycle includes a distance between two consecutive peaks in a trajectory of a joint.

15. The system for gait analysis as set forth in claim 13, wherein the gait cycle includes a distance between consecutive peaks in an angle of a joint or body part.

16. A non-transitory computer-usable medium for gait analysis of a subject, said computer-usable medium embodying a computer program code, said computer program code comprising computer executable instructions configured for:

obtaining visual data from the image capture device, the image capture device being positioned in front of at least one walking subject, the image capture device including a camera mounted in an elongate hallway in which the plurality of subjects can walk towards the camera, said visual data including a frontal view of the subject approaching the camera, the visual data comprising at least two image frames of the at least one walking subject over a period of time walking toward the image capture device, the at least two image frames capturing at least a portion of the gait of the at least one walking subject;

analyzing the visual data to determine the identity of the at least one walking subject;

for each identified walking subject:

segmenting one or more gait cycles of the identified walking subject, the segmenting including detecting within the at least two images body parts as two-dimensional landmarks using a pose estimation algorithm on each of the at least two frames, generating a joint model depicting the location of the at least one joint in each of the at least two frames, and using the joint model to segment the one or more gait cycles;

detecting at least one gait feature in the one or more gait cycles;

comparing the at least one gait feature to at least one of the following to detect an abnormal gait: a threshold value or a history of gait cycles of the identified walking subject;

repeating the foregoing steps over a period of time to generate a gait profile for each identified walking subject.

\* \* \* \* \*